Figure 1:
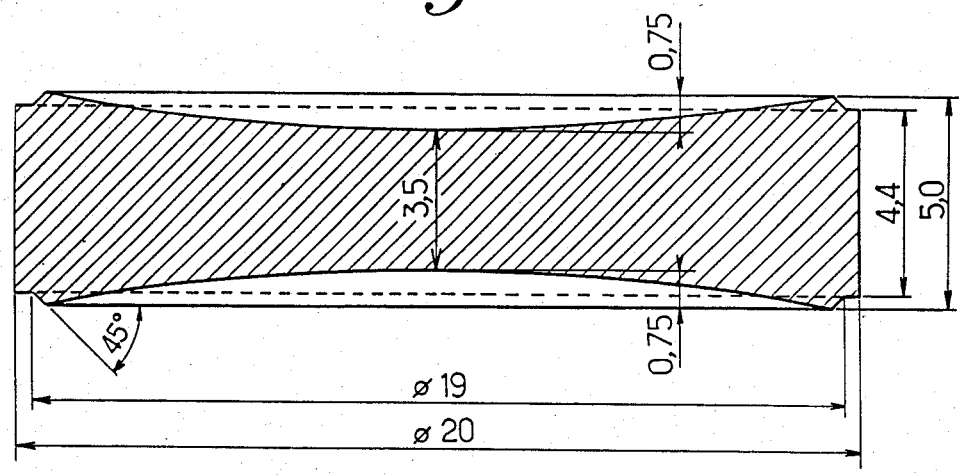

United States Patent [19]

Serpelloni et al.

[11] Patent Number: 4,661,647

[45] Date of Patent: Apr. 28, 1987

[54] DIRECTLY COMPRESSIBLE GRANULAR MANNITOL AND METHOD FOR ITS MANUFACTURE

[75] Inventors: Michel Serpelloni, Bethune; Patrick Lemay, Lestrem, both of France

[73] Assignee: Roquette Freres, Lestrem, France

[21] Appl. No.: 786,859

[22] Filed: Oct. 11, 1985

[51] Int. Cl.⁴ .................. C07C 29/78; C07C 31/26
[52] U.S. Cl. ................. 568/868; 568/852; 422/245
[58] Field of Search ................. 568/868, 852

[56] References Cited

U.S. PATENT DOCUMENTS

| | | | |
|---|---|---|---|
| 2,315,699 | 4/1943 | Goepp | 568/868 |
| 2,594,863 | 4/1952 | Buck et al. | 568/868 |
| 3,308,171 | 3/1967 | Oikana | 568/868 |
| 3,330,874 | 7/1967 | Shannon | 568/868 |
| 3,341,415 | 9/1967 | Scott | 167/82 |
| 3,484,492 | 12/1969 | Hales | 568/868 |
| 3,632,656 | 1/1972 | Unver | 568/868 |
| 4,293,570 | 10/1981 | Vadasz | 568/868 |
| 4,507,511 | 3/1985 | Reiff et al. | 568/868 |

FOREIGN PATENT DOCUMENTS

| | | | |
|---|---|---|---|
| 554859 | 3/1958 | Canada | 568/868 |
| 16085 | 5/1977 | Japan | 568/868 |
| 1481846 | 8/1977 | United Kingdom | 568/868 |

Primary Examiner—J. E. Evans
Attorney, Agent, or Firm—Larson and Taylor

[57] ABSTRACT

The invention relates to a granular mannitol directly compressible and free from binder, characterized by the fact that its granulometric fraction from 400 to 500 μm has a friability less than 65% in a test A.

12 Claims, 2 Drawing Figures

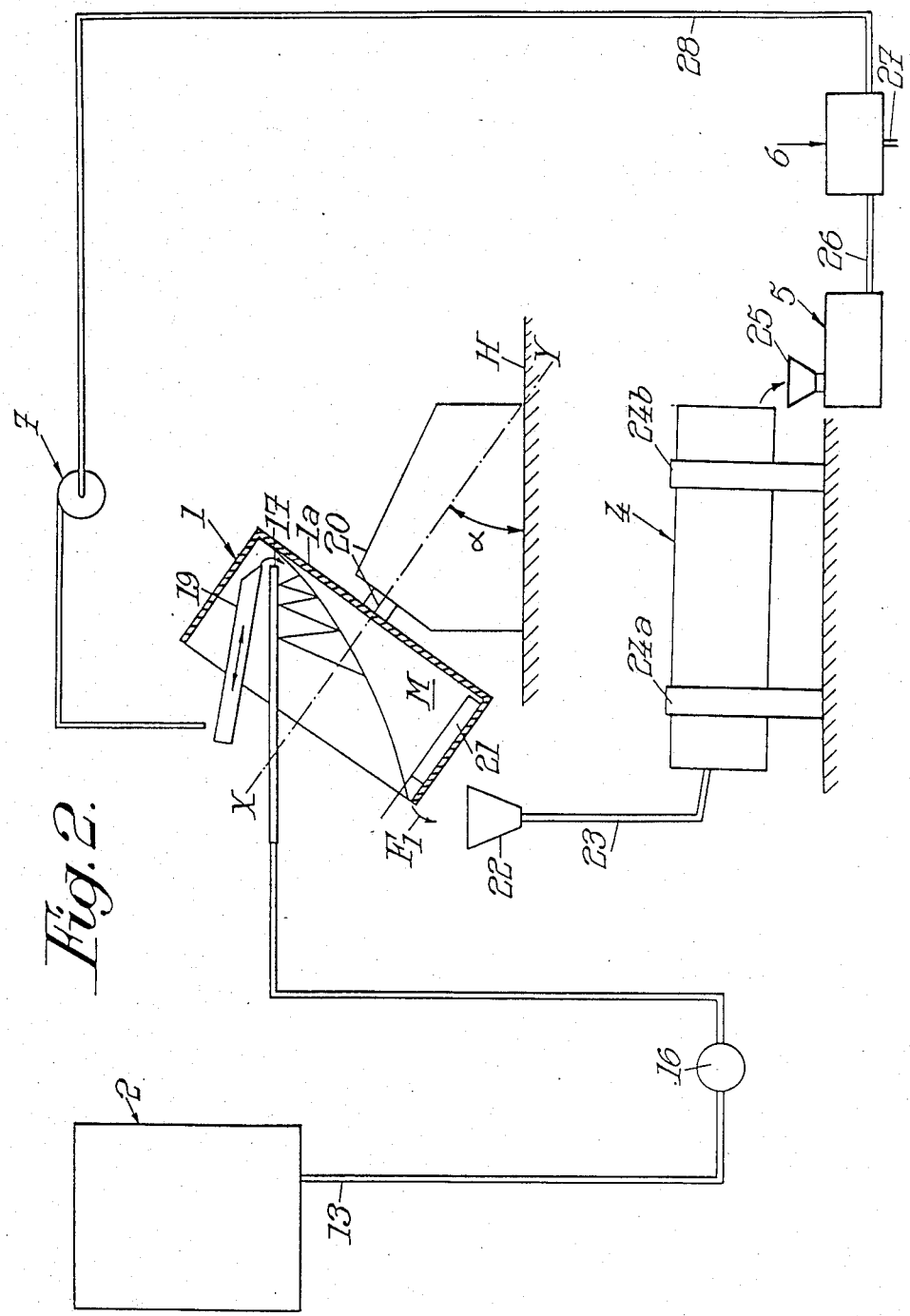

DIRECTLY COMPRESSIBLE GRANULAR MANNITOL AND METHOD FOR ITS MANUFACTURE

The invention relates to a directly compressible granular mannitol.

It is directed also to a process for manufacturing this mannitol.

Mannitol, for its taste and low hygroscopicity constitutes a pharmaceutical excipient of quality when it is made directly compressible; now, it does not have this property naturally, particularly when it is obtained by crystallisation in water; it is, besides, naturally very friable and consequently undergoes considerable crumbling during shipment; such crumbling produces fine particles which have a deleterious effect on its capacity for flow and on the compressibility.

It follows that the properties of directly compressible granular mannitol to be found in the trade are not satisfactory.

In this case, the friability and the compressibility are very far from those of the pharmaceutical excipient which is customarily taken as reference, namely lactose which can be directly compressible but which exhibits precisely defects from which mannitol is free, namely:
too great a hygroscopicity,
reducing power,
too great cariogenicity.

It has already been attempted to overcome these drawbacks by incorporating a binder with the mannitol.

But the presence of a binder is not much appreciated by the user.

There existed, consequently, a need for a granular mannitol of very little friability, hence easily transportable, and directly compressible, not including a binder and comparable or even outclassing granular lactose without granulation binder.

It is this need that the Applicants have attempted to satisfy.

Now, they had the merit of finding that it was possible to prepare a binderless directly compressible granular mannitol, of substantially lower friability than that of all known directly compressible mannitols, including those comprising a binder.

This directly compressible mannitol without binder is a novel industrial product and constitutes the principal feature of the invention.

According to one aspect of the invention, the aforesaid directly compressible and binderless mannitol, is characterized by the fact that it shows a friability below 65% in a test A.

This mannitol shows, simultaneously with this low friability, a compressibility higher than 49.0N, preferably than 78.4N in a test B.

In addition, it has an excellent flow index, greater than 65% in a test C.

The friability manifests the crushing resistance of the mannitol granules.

It is illustrated by the proportion of granules which, after crushing, is not retained by a sieve of given mesh width, that is to say has undergone a reduction in the dimensions of the particles such that the latter can pass through the meshes of said sieve.

To evaluate the friability, recourse can be had to test A.

The latter consists of subjecting the granules to be tested to crushing done in an apparatus named a friabilimeter; in the test A was used the brand "ERWEKA TAP" friabilimeter manufactured by the ERWEKA Company (6056 Heusenstamm Federal Republic of Germany of FRG which revolves at a uniform rotary speed of 25 rpm, and into which have been inserted 5 identical steel balls of 17 mm diameter and 18.87 g weight.

Into the crushing chamber of the friabilimeter was introduced an amount of 15 g granules corresponding to the granulometric fraction of 400 to 500 $\mu$m; the apparatus was placed in rotation for 15 minutes.

At the end of the experiment, the proportion by weight represented by the residue retained on a sieve of mesh width 351 microns was determined.

The value of the friability corresponds to the percentage of powder not retained by the previously defined sieve.

Friability is all the lower as the percentage of powder unretained by the above-said sieve is less.

For the measurement of the compressibility, recourse may be had to test B which consists of manufacturing by means of a high yield rotary press, tablets and of measuring the breakage strength thereof.

The press used is a type P 1000 press manufactured by the WILHELM FETTE Company (2053 Schwarzenbeck F.R.G.); it is equipped with measuring gauges for the forces of compression and ejection.

The tablets prepared are round, biconcave, 20 mm in diameter and 5 mm thickness; their shape and their dimensions are those appearing in FIG. 1, which is a diametric section of a tablet prepared from a powder of the product to be tested.

The compression pressure applied was 196, 133 MPa and the powdered mannitol used was supplemented with a lubricant, in the event magnesium stearate, in an amount such that the ejection force remains less than 500 Newtons (N), the observed conditions for sound operation of the equipment.

The compressibility, expressed by the value of the breaking strength, in Newtons, was measured by means of an ERWEKA TB 24 durometer, equipped with a tablet support trestle or stand, having a distance between supports of 10.55 mm.

For the measurement of the flow index, a test C may be resorted to which provides in fact what is called the CARR index; the test C is described in Chem. Eng. 72, No. 1, 163–168 (1965) and Chem. Eng. 72, No. 2, 69–73 (1965).

It is possible to use in this repsect the apparatus marketed by the HOSOKAWA Company under the brand "Powder Tester".

In the examples which will be described below, there are provided, for the directly compressible granular products tested (mannitol according to the invention, mannitol of the prior art, lactose) also other magnitudes, namely:
the granulometric distribution, and the average granulometry,
the value of the specific surface,
the value of the porosity.

The average granulometry (average size corresponding to 50% of the distribution in the mass) presented by the mannitol according to the invention may be less than 650 $\mu$m, thus favoring its use in the preparation of pharmaceutical tablets weakly dosed with active principles.

The friability manifests the breaking strength of the mannitol granules.

The "specific surface" is expressed in $m^2$ per g of product. It is measured by the well-known method of BET (see Techniquesde l'Ingénieur, 1968, vol. 5, p. 3645, lines 1–11).

Porosity is expressed in $cm^3/g$. It is measured by porosimetry with mercury (see op. cit. Techniques de l'Ingénieur).

To prepare the directly compressible and binderless granular mannitol according to the invention, recourse may be had, still according to the invention, to a method characterized by the fact that into an open vessel, of horizontal axis or inclined to the horizontal, rotated around said axis at a speed of 2 to 10 rpm, containing a mass of mannitol granules at a temperature 145° to 165° C., kept in motion by the rotation of the vessel, there is introduced simultaneously and continuously on the one hand, crystalline mannitol of granulometry less than 5 mm, preferably less than 1.5 mm, and of a temperature from 5° to 150° C., preferably from 50° to 150° C.

on the other hand, mannitol essentially in the liquid state, divided or not into droplets of dry matter content higher than 98% and of a temperature comprised between 164° and 180° C. and, preferably from 166.5° to 180° C., and more advantageously still from 175° to 180° C.

the crystalline mannitol and the liquid mannitol being brought to the surface of the mass of granules in motion in a ratio of 6 to 1.5 parts by weight of liquid mannitol per 1 part by weight of crystalline mannitol, these parameters being selected within the given limits so that total fusion does not occur at the surface of the mass in motion where the mannitol essentially in the liquid state and the crystalline mannitol meet, the large size granules which have a tendency to rise to the surface of the mass in motion through a segregation phenomenon, being collected, for example, by overflowing towards the outside of the rotary vessel.

Preferably, these granules are subject to a ripening phase by keeping at a temperature of 70° to 80° C. for 5 to 60 minutes.

Proposing, consequently, to manufacturing directly compressible, granular mannitol, according to the invention, procedure is as follows or in the equivalent manner.

The raw materials used within the scope of the method according to the invention comprise:

mannitol essentially in the liquid state kept at a temperature of about 164° to 180° C., preferably from 166.5° to 180° C., and more advantageously still from 175° to 180° C., and crystalline mannitol of a granulometry less than 5 mm and, preferably than 1.5 mm and of a temperature from about 5° to 150° C., preferably from 50° to 150° C.

These two constituents, namely, liquid mannitol and crystalline mannitol are introduced continuously in the respective proportions of about 6 to 1.5 parts by weight for the first and about 1 part by weight for the second, into an open vessel of horizontal axis or inclined to the horizontal rotated around said axis at a speed of 2 to 10 rpm and containing a mass of mannitol granules kept in motion by the rotation of the vessel and at a temperature of 145° to 165° C. by suitable means, the mixture of liquid mannitol and crystalline mannitol being formed at the surface of the mass in motion; this motion recalls that of a mass of sugar coated pills or candies inside a candy-making vessel and it is due to it that granules are formed of larger and larger size, the granules of larger size having the tendency to come to the surface of the mass in motion.

The liquid mannitol which was prepared, for example, by fusion of powdered mannitol in an installation arranged so that any overheating is avoided is brought to the surface of this mass in motion in the state of bundles, of sheets, of filaments and preferably in a finely divided state in the form of droplets by means, for example, of spraying means.

All of the parameters are selected so that inside the vessel and at the surface of the mass in motion, total fusion of the constituent granules of the mass cannot occur.

These granules collected by overflow are constituted by an agglomerate of fused mannitol and crystalline mannitol powder; they are, preferably, subjected to a ripening treatment for about 5 to 60 minutes at a temperature of about 70° to 80° C.

They are then ground, for example by means of a grinder of the hammer crusher type.

The particles of granulometry less than about 5 mm and, preferably less than 1.5 mm, are generally recycled and constitute a porton of the crystalline raw material employed.

The installation for employing the method which has just been described comprises essentially, as results from the diagrammatic section shown in FIG. 2, a rotary vessel denoted as a whole by 1 and whose axis XY has, as the case may require, an inclination to the horizontal; this vessel is placed in series, as shown in FIG. 1 with, upstream:

a supply device 2 for mannitol in the essentially liquid state, means for dispersing the liquid mannitol inside the vessel 1 and means adapted to mix with the dispersed, fused mannitol, crystalline mannitol of granulometry less than 5 mm and, donwstream of the vessel 1:

preferably, a rotary "ripening" vessel 4, a grinding installation 5, a sifting installation 6, means 7 adapted to recycle to the outlet of the sifting installation and to the mixing means cooperating with the vessel 1, the portion of the ground crystalline mannitol of fine granulometry.

The device 2 is connected to the rotary vessel 1 through a pipe 13 provided with a pump 16.

The preferred means for dispersing liquid mannitol comprise the pump 16 bringing to the level of vessel 1 liquid mannitol and spraying it by means of a nozzle 17, for example, in the form of a ramp, placed in the vicinity of the bottom 1a of the vessel. The droplets of sprayed liquid mannitol are brought into the presence of powdered crystalline mannitol introduced, for example, by means of a device 19 of the vibrating distributor type.

The mixing is effected at the surface of the mass M in motion which partly fills the vessel as shown.

The rotation of the latter is ensured, for example, by a driving device shown diagrammatically at 20.

The vessel 1 may be constructed in the form of a vat or drum, as shown in FIG. 2.

It is also possible to construct it similarly to a candy-making tub, that is to say in the form of a sphere from which a portion has been removed.

When the vessel 1 has a shape similar to that shown in FIG. 1, an angle of inclination generally higher than 25° is used and, preferably, comprised between 25° and 45°.

Means (not shown) are then provided to vary said inclination of the axis of rotation XY to the horizontal plane.

When the vessel 1 has the shape of a candy-making tub, the inclination may be less than 25° and even become nil.

Advantageously, the vessel 1 is equipped with a scraper blade 21.

The granules which are brought to the surface of the mass in motion M are removed from the vessel 1, for example, along an overflow system (see the arrow $F_1$) and conducted thus to a chute 22 which is connected through a pipe 23 to the entrance of the rotary cylinder 4 advantageously included in the installation. This rotary cylinder 4 is supported by the bearings 24a and 24b comprising means adapted to rotate it. The dimensions of this cylinder, its rotary speed and its inclination are selected so that the duration of dwell of a given granule inside this cylinder is comprised preferably between 5 and 60 minutes.

At the exit of the rotary cylinder 4, the ripened granules and, consequently, constituted by crystalline mannitol, fall into a chute 25 and are introduced into the above-said grinding installation 5. This installation is, preferably, arranged so that it is possible to vary the granulometry of the ground product obtained.

At the exit from this grinding installation, the ground product is led through a pipe 26, equipped preferably with pneumatic conducting means, to the sifting installation 6 at the outlet of which there are collected, on the one hand, the product having the desired granulometry which is removed through a pipe 27 and, on the other hand, product of too small a granulometry which is recycled through a pipe 28 to the vessel 1, said pipe 28 including means 7 mentioned above which are constituted, for example, by a turbine.

This being the case, to fix ideas, it is indicated that, in an installation giving good results and which has been used experimentally by the Applicants, a vessel 1 in the form of a tank of the type of that shown in FIG. 1, of diameter 3.60 m and depth 1.20 m and whose inclination is adjustable between 25° and 45° was used; in general a rotary speed of about 7 rpm is imparted to this tank. In this same installation, a cylinder 4 was used whose length was 8.50 m, diameter 1.80 m, inclination 5° and rotary speed 10 rpm.

To illustrate the foregoing, below are given examples of the preparation of directly compressible granular mannitol according to the invention by employing the method and the installation according to the invention.

EXAMPLE 1

The supply of the installation described was undertaken at the rate of 375 kg/hour with powdered mannitol of average granulometry 120 microns and 800 kg/hour of fused mannitol, at 175° C., and the inclination of the vessel 1 was adjusted to a value of 30°.

The temperature existing within the mass of granules in motion was 160° to 165° C.

The average dwell time in the ripening vessel was 25 minutes.

The average size of the granules recovered by overflow was 5 to 15 mm.

The directly compressible granular mannitol so obtained had the following characteristics:

| | |
|---|---|
| granulometric distribution | $>1000\ \mu m$: 0.5%<br>$>500\ \mu m$: 48%<br>$>250\ \mu m$: 99% |
| average granulometry | 520 microns |
| breakage strength (expressed in Newtons, "ERWEKA" apparatus) | 97.0 |
| friability | 45% |
| flow | 85 |
| specific surface | $<0.4\ m^2/g$ |
| porosity in $cm^3/g$ | $<1.$ |

EXAMPLE 2

Procedure was as shown in Example 1 but by modifying the following parameters; the inclination of the vessel 1 changed to a value of 35°.

The granules recovered by overflow had an average granulometry of 5 to 10 mm and were directly subjected to grinding.

The directly compressible granular mannitol thus obtained had the following characteristics:

| | |
|---|---|
| granulometric distribution | $>1000\ \mu m$: 3%<br>$>500\ \mu m$: 73%<br>$>250\ \mu m$: 99% |
| average granulometry | 620 microns |
| breakage strength (expressed in Newtons, "ERWEKA" apparatus) | 91.2 |
| friability | 45% |
| flow | 85 |
| specific surface | $<0.4\ m^2/g$ |
| porosity in $cm^3/g$ | $<1.$ |

In the table, there are collected the granulometry, compressibility, friability and flow characteristics:
of the mannitols of examples 1 and 2,
of a commercial directly compressible lactose,
of a commercial binderless directly compressible mannitol,
of a directly compressible mannitol including a binder.

TABLE

| | Directly compressible Lactose | Mannitol according to Example 1 | Mannitol according to Example 2 | Binderless commercial directly compressible Mannitol | Directly compressible Mannitol with binder (1.5% of gelatin) |
|---|---|---|---|---|---|
| Granulometric $>1000\ \mu m$ | 0 | 0.5 | 3 | 8.1 | 3 |
| distribution in % $>500\ \mu m$ | 0 | 48 | 73 | 95 | 77 |
| cumulated by weight $>250\ \mu m$ | 3 | 99 | 99 | 99 | 99 |
| Average granulometry (in $\mu m$)* | 90 | 520 | 620 | 860 | 650 |
| Content in % of magnesium stearate | 1 | 0.5 | 0.5 | 0.8 | 1 |
| Breaking strength (in Newtons) | 85.3 | 97.0 | 91.2 | 59.8 | 130.4 |
| Friability (expressed in %) | ** | 45 | 45 | 81 | 70 |

TABLE-continued

| | Directly compressible Lactose | Mannitol according to Example 1 | Mannitol according to Example 2 | Binderless commercial directly compressible Mannitol | Directly compressible Mannitol with binder (1.5% of gelatin) |
|---|---|---|---|---|---|
| Flow (Carr index) | 83 | 85 | 85 | 82 | 85 |

*average granulometry, corresponds to 50% of the distribution by weight
**non measureable by the test indicated The superiority of the directly compressible mannitol according to the present invention appears clearly on examining the results collected in the present table.

Its friability has a value so low that it is fundamentally different with respect to that of existing directly compressible mannitol, even with binders; the shipment of the directly compressible granular mannitol according to the invention therefore poses hardly any problem from the point of view of crumbling and formation of troublesome fine particles.

Its compressibility is higher than that of lactose.

Its flow index, equal to or greater than that of lactose and of directly compressible commercial mannitol with or without binder, is sufficiently high for commercial exploitation as excipient for direct compression to be adoptable.

All these values are obtained for a lower average ganulometry than that of known directly compressible mannitol, with or without binder, which destines the mannitol according to the invention to the manufacture of pharmaceutical tablets weakly dosed with active principles.

As is self evident and as results besides already from the foregoing, the invention is in no way limited to those of its types of application and embodiments which have been more particularly envisaged; it encompasses, on the contrary, all modifications.

We claim:

1. Directly compressible granular mannitol free from granulation binder, characterized by the fact that its granulometric fraction of 400 to 500 μm has a friability less than 65% in a test A, said test A consisting in subjecting a given amount of mannitol granules whose granulometry is comprised ebtween 400 and 500 μm to crushing in a friabilimeter, the thus crushed mannitol granules being passed through a sieve having a mesh width of 351 μm leaving, retained on the sieve, a residue representing a proportion in percent by weight of the given amount of granules subjected to crushing, the proportion in percent by weight of the given amount not retained on the sieve representing the friability.

2. Directly compressible granular mannitol free from granulation binder according to claim 1, characterized by the fact that it has a compressibility higher than 49.0N in a test B, said test B consisting in preparing tablets from said granular mannitol and in measuring the breakage strength thereof which breakage strenght is representative of the compressibility of the granular mannitol, the preparation of the tablets which are round, biconcave, 20 mm in diameter and 5 mm in thickness, comprising adding lubricant to the granular mannitol and compressing in the thus obtained mixture in a high yield rotary press under a compression pressure of 196, 133 MPa, the said press being equipped with measuring gauges for the forces of compression and ejection and the amount of lubricant added to the granular mannitol being such that the ejection force remains less than 500 Newtons, the measuring of the breakage strength, expressed in Newtons, of the thus prepared tablets, being done by means of a durometer equipped with a tablet support trestle having a distance between supports of 10.55 mm.

3. Directly compressible granular mannitol free from granulation binder according to claim 1, characterized by the fact that it has a compressibility higher than 78.4N in a test B, said test B consisting in preparing tablets from said granular mannitol and in measuring the breakage strength thereof which breakage strenght is representative of the compressibility of the granular mannitol, the preparation of the tablets which are round, biconcave, 20 mm in diameter and 5 mm in thickness, comprising adding lubricant to the granular mannitol and compressing in the thus obtained mixture in a high yield rotary press under a compression pressure of 196, 133 Mpa, the said press being equipped with measuring gauges for the forces of compression and ejection and the amount of lubricant added to the granular mannitol being such that the ejection force remains less than 500 Newtons, the measuring of the breakage strength, expressed in Newtons, of the thus prepared tablets, being done by means of a durometer equipped with a tablet support trestle having a distance between supports of 10.55 mm.

4. Directly compressible granular mannitol free from granulation binder according to claim 1, characterized by the fact that it has a compressibility higher than 49.0N in a test B, said test B consisting in preparing tablets from said granular mannitol and in measuring the breakage strength thereof which breakage strenght is representative of the compressibility of the granular mannitol, the preparation of the tablets which are round, biconcave, 20 mm in diameter and 5 mm in thickness, comprising adding lubricant to the granular mannitol and compressing in the thus obtained mixture in a high yield rotary press under a compression pressure of 196, 133 Mpa, the said press being equipped with measuring gauges for the forces of compression and ejection and the amount of lubricant added to the granular mannitol being such that the ejection force remains less than 500 Newtons, the measuring of the breakage strength, expressed in Newtons, of the thus prepared tablets, being done by means of a durometer equipped with a tablet support trestle having a distance between supports of 10.55 mm, the said mannitol being further characterized by the fact that it has a flow index higher than 65 in a test C as described in Chem. Eng. 72, No. 1, 163–168 (1965).

5. Directly compressible granular mannitol free from granulation binder according to claim 1, characterized by the fact that it has a compressibility higher than 78.4N in a test B, said test B consisting in preparing tablets from said granular mannitol and in measuring the breakage strength thereof which breakage strenght is representative of the compressibility of the granular mannitol, the preparation of the tablets which are round, biconcave, 20 mm in diameter and 5 mm in thickness, comprising adding lubricant to the granular mannitol and compressing in the thus obtained mixture in a high yield rotary press under a compression pressure of 196, 133 Mpa, the said press being equipped with measuring gauges for the forces of compression and ejection and the amount of lubricant added to the granular mannitol being such that the ejection force remains less than 500 Newtons, the measuring of the breakage strength, expressed in Newtons, of the thus prepared tablets, being done by means of a durometer equipped with a tablet support trestle having a distance between supports of 10.55 mm, the said mannitol being further characterized by the fact that it has a flow index higher than 65 in a test C as described in Chem. Eng. 72, No. 1, 163–168 (1965).

6. Directly compressible granular mannitol free from granulation binder according to claim 1, characterized by the fact that it has a compressibility higher than 49.0N in a test B, said test B consisting in preparing tablets from said granular mannitol and in measuring the breakage strength thereof which breakage strenght is representative of the compressibility of the granular mannitol, the preparation of the tablets which are round, biconcave, 20 mm in diameter and 5 mm in thickness, comprising adding lubricant to the granular mannitol and compressing in the thus obtained mixture in a high yield rotary press under a compression pressure of 196, 133 Mpa, the said press being equipped with measuring gauges for the forces of compression and ejection and the amount of lubricant added to the granular mannitol being such that the ejection force remains less than 500 Newtons, the measuring of the breakage strength, expressed in Newtons, of the thus prepared tablets, being done by means of a durometer equipped with a tablet support trestle having a distance between supports of 10.55 mm, the said mannitol being further characterized by the fact that it has a flow index higher than 65 in a test C as described in Chem. Eng. 72, No. 1, 163–168 (1965) and by the fact that it has an average granulometry (average size corresponding to 50% of the distribution by weight) less than 650 µm facilitating its use in the preparation of pharmaceutical tablets weakly dosed with active principles.

7. Directly compressible granular mannitol free from granulation binder according to claim 1, characterized by the fact that it has a compressibility higher than 78.4N in a test B, said test B consisting in preparing tablets from said granular mannitol and in measuring the breakage strength thereof which breakage strenght is representative of the compressibility of the granular mannitol, the preparation of the tablets which are round, biconcave, 20 mm in diameter and 5 mm in thickness, comprising adding lubricant to the granular mannitol and compressing in the thus obtained mixture in a high yield rotary press under a compression pressure of 196, 133 Mpa, the said press being equipped with measuring gauges for the forces of compression and ejection and the amount of lubricant added to the granular mannitol being such that the ejection force remains less than 500 Newtons, the measuring of the breakage strength, expressed in Newtons, of the thus prepared tablets, being done by means of a durometer equipped with a tablet support trestle having a distance between supports of 10.55 mm, the said mannitol being further characterized by the fact that it has a flow index higher than 65 in a test C as described in Chem. Eng. 72, No. 1, 163–168 (1965) and by the fact that it has an average granulometry (average size corresponding to 50% of the distribution by weight) less than 650 µm facilitating its use in the preparation of pharmaceutical tablets weakly dosed with active ingredients.

8. Method to prepare directly compressible granular mannitol free from granulation binder, of friability less than 65% in a test A consisting in subjecting a given amount of mannitol granules whose granulometry is comprised between 400 and 500 µm to crushing in a friabilimeter, the thus crushed mannitol granules being passed through a sieve having a mesh width of 351 µm leaving, retained on the sieve, a residue representing a proportion in percent by weight of the given amount of granules subjected to crushing, the proportion in percent by weight of the given amount not retained on the sieve representing the friability, said method being characterized by the fact that into an open vessel, of horizontal axis or inclined to the horizontal, rotated around said axis at a speed of 2 to 10 rpm, containing a mass of mannitol granules at a temperature 145° to 165° C., kept in motion by the rotation of the vessel, there is introduced simultaneously and continuously on the one hand, crystalline mannitol of granulometry less than 5 mm, preferably less than 1.5 mm, and of a temperature from 5° to 150° C., preferably from 50° to 150° C., on the other hand, mannitol essentially in the liquid state, divided or not into droplets of dry matter content higher than 99% and of a temperature comprised between 164° and 180° C., the crystalline mannitol and the liquid mannitol being brought to the surface of the mass of granules in motion in a ratio of 6 to 1.5 parts by weight of liquid mannitol per 1 part by weight of crystalline mannitol, these parameters being selected within the limits indicated so that total fusion at the surface of the mass in motion does not occur where the mannitol essentially in the liquid state and the crystalline mannitol meet, the granules of large size which have a tendency to rise to the surface of the mass in motion by a segregation phenomenon being collected preferably by overflow to the outside of the rotary vessel.

9. Method according to claim 1, characterized by the fact that the granules collected at the exit from the vessel 1 being subjected to a ripening phase by maintaining them at a temperature of 70° to 80° C. for 5 to 60 minutes.

10. Directly compressible mannitol characterized by the fact that it has been prepared by the process according to claim 8.

11. Directly compressible mannitol characterized by the fact that it has been prepared by the process according to claim 9.

12. Method according to claim 8, wherein the mannitol introduced essentially in the liquid state is at a temperature between 166.5° and 180° C.

* * * * *